US010402536B2

(12) United States Patent
Herbst et al.

(10) Patent No.: US 10,402,536 B2
(45) Date of Patent: *Sep. 3, 2019

(54) PREPOPULATING CLINICAL EVENTS WITH IMAGE BASED DOCUMENTATION

(71) Applicant: CERNER INNOVATION, INC., Kansas City, KS (US)

(72) Inventors: Damon Herbst, Shawnee, KS (US); Carla Leighow, Grain Valley, MO (US); David A. Robaska, Parkville, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 447 days.

This patent is subject to a terminal disclaimer.

(21) Appl. No.: 13/957,627

(22) Filed: Aug. 2, 2013

(65) Prior Publication Data

US 2013/0317857 A1 Nov. 28, 2013

Related U.S. Application Data

(63) Continuation of application No. 12/982,151, filed on Dec. 30, 2010, now Pat. No. 8,548,826.

(51) Int. Cl.
*G16H 30/20* (2018.01)
*G06F 19/00* (2018.01)
*G06Q 10/10* (2012.01)
*G06Q 50/24* (2012.01)

(52) U.S. Cl.
CPC .......... *G06F 19/321* (2013.01); *G06Q 10/10* (2013.01); *G06Q 50/24* (2013.01)

(58) Field of Classification Search
CPC .............................. G06F 19/321; G16H 30/20
USPC ............................................................ 705/3
See application file for complete search history.

(56) References Cited

U.S. PATENT DOCUMENTS

| 6,148,117 | A | * | 11/2000 | Lopez | G06T 3/403 |
| | | | | | 382/263 |
| 2004/0026501 | A1 | * | 2/2004 | Walsh | A61N 5/1048 |
| | | | | | 235/380 |
| 2006/0122865 | A1 | * | 6/2006 | Preiss | G06Q 10/0633 |
| | | | | | 705/2 |
| 2009/0182577 | A1 | * | 7/2009 | Squilla | G06O 10/06 |
| | | | | | 705/2 |
| 2011/0238437 | A1 | * | 9/2011 | Zhou | G06F 19/3487 |
| | | | | | 705/2 |

* cited by examiner

*Primary Examiner* — John A Pauls
(74) *Attorney, Agent, or Firm* — Shook, Hardy & Bacon L.L.P.

(57) ABSTRACT

Systems, methods, and computer-readable media having computer-executable instructions embodied thereon for protocol driven image acquisition are provided. In embodiments, a protocol is received by an image capturing device. The protocol comprises orders from a clinician, a workflow for capturing at least one image, or a combination thereof. At least one field for receiving metadata to be associated with the at least one image allows structured documentation to begin on the image capturing device. The at least one image and associated metadata are communicated to a medical information system. A patient is identified by the metadata or an existing patient to device association and the at least one image is associated with an electronic medical record for the patient.

20 Claims, 8 Drawing Sheets

PREPOPULATING CLINICAL EVENTS WITH IMAGE BASED DOCUMENTATION

RELATED APPLICATIONS

This patent application is a continuation of and claims priority to U.S. patent application Ser. No. 12/982,151, filed Dec. 30, 2010, which is incorporated herein by reference in the entirety.

BACKGROUND

In recent years, healthcare service providers have been making the transition from manual paper-based medical records to an electronic format. Commercially available computer software, such as PowerChart®, PowerChart Office®, and other Cerner Millennium® applications marketed by Cerner Corporation of Kansas City, Mo. have advanced the state of the art well beyond the conventional manual approach. Electronic-based records substantially increase the efficiency of healthcare providers and institutions. Electronic medical records also substantially reduce risks associated with high volumes of patient data and potential liabilities arising out of clerical errors or misinformation. The electronic format enhances communication between various providers and within institutions. As electronic clinical documentation continues to become increasingly prevalent, the variety of applications, electronic forms, electronic charts, and user interfaces, as well as the corresponding versatility of this format, continue to expand.

Images are commonly used by physicians and other healthcare providers to memorialize relevant image-related information associated with patient interactions. In many cases, images provide great insight into the patient interaction, particularly when accompanied by supporting documentation. For example, the patient may be a burn victim or have a broken bone. Images are often captured by someone other than a physician and orders must be sent from the person responsible for capturing the images (hereinafter, the "photographer"). Images can be captured in many forms, such as by a digital camera, a handheld scanner, or other medical imaging device. Hard-copy images can be mislabeled or lost, and are not an efficient means of preserving image data that is to accompany medical records. Even electronic image files present challenges as they still must be imported, attached, or otherwise appended to existing records. Similar problems can arise with misidentification and mishandling of these unassociated electronic files within vast medical information systems.

Many currently available forms of image capturing devices are limited in their ability to add image related documentation to the image file. For example, conventional digital cameras do not allow a user to associate clinical documentation with the actual image. Similarly, conventional image capturing devices do not integrate with protocols to provide the user with a set of instructions to fulfill the clinician's orders. In addition, conventional electronic medical records are unable to associate an image with a specific portion of a patient's medical record.

SUMMARY

Embodiments of the present invention relate to systems, methods, and computer-readable media having computer-executable instructions embodied thereon for performing a method in a computerized healthcare system, and computer systems for medical image acquisition and documentation.

In one embodiment, the method includes decoding a barcode associated with a patient. The barcode includes information associated with the patient. At least one field is populated with metadata derived from the information. At least one image of the patient is then captured and the metadata is associated with the at least one image.

In one embodiment, the method includes communicating a protocol to an image capturing device for taking at least one image of a patient. The protocol comprises orders from a clinician, a workflow for capturing the at least one image, or a combination thereof. The at least one image and the associated metadata are received into a medical information system. A stored patient associated with the associated metadata is identified. The at least one image and associated metadata is stored in an electronic medical record for the patient.

In one embodiment, the method includes receiving a protocol for capturing at least one image of a patient. Information associated with the patient is received. A protocol for capturing the at least one image of the patient is displayed. At least one field is populated with metadata corresponding to the patient. The metadata is associated with the at least one image and is transmitted, along with the image, to an electronic medical record ("EMR") associated with the patient.

In one embodiment, the method includes monitoring a repository for an indication that at least one image has arrived. At least one image is received from the repository. Metadata is extracted from the at least one image and is used to identify at least one patient. The at least one image and the corresponding metadata are associated with an EMR for the at least one patient. At least one image is displayed in the EMR for the at least one patient.

In one embodiment, at least one image of a patient is received. A patient attributed is extracted from the at least one image and a photo type is identified based on the photo attribute. The at least one image is sorted utilizing the patient attribute, a patient identification, or a combination thereof. At least one image is displayed in the EMR associated with the patient.

In one embodiment, at least one image of a patient is acquired from an image capturing device. A body part associated with the at least one image is identified as a tag. The tag is stored as metadata associated with the at least one image. The at least one image is indexed according to the tag. After a tag is selected for reviewing a body area, the at least one selected image for the selected tag is displayed.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide systems, methods, and computer-readable media having computer-executable instructions embodied thereon for protocol driven image acquisition, populating an EMR with images, and beginning structured documentation on an image capturing device. An exemplary operating environment is described below, though one of ordinary skill in the art will appreciate that other suitable operating environments may be used.

Figure 1:
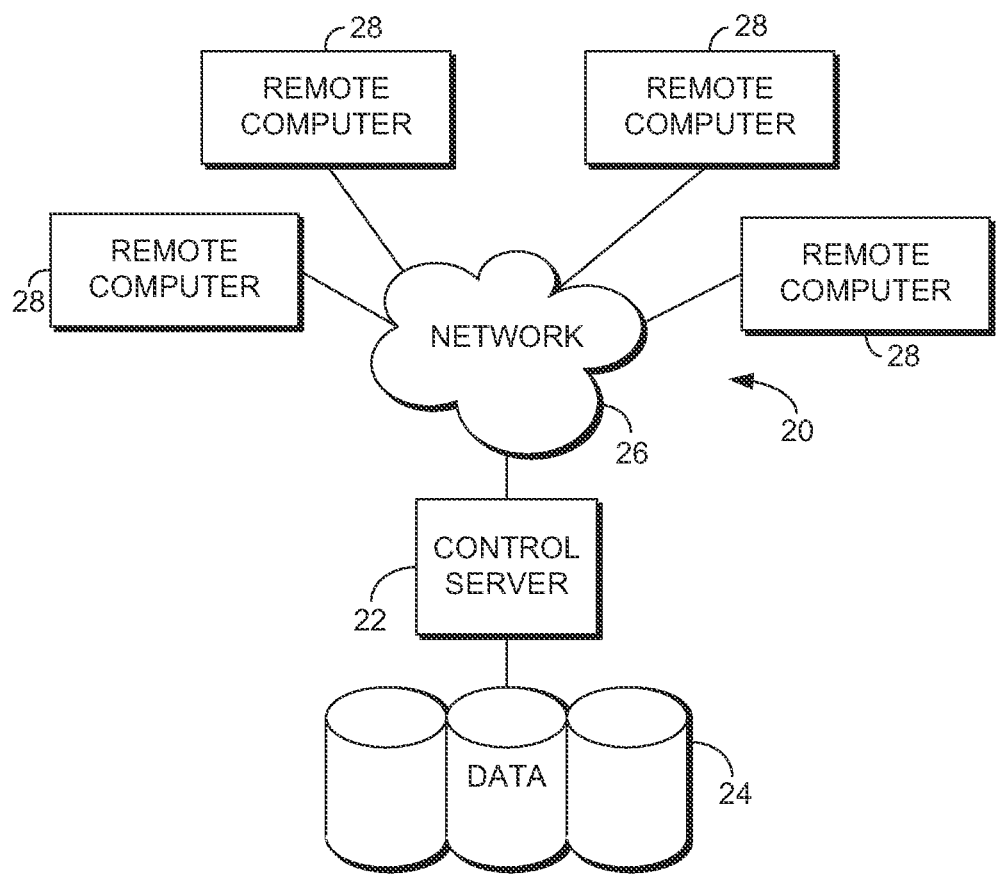
FIG. 1 is a block diagram of an exemplary computing system suitable for use in implementing embodiments of the present invention.

Referring now to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22. For example, the database cluster 24 can contain electronic clinical documents capable of receiving multiple types of input, including images, dictation audio input, structured user input, free-text input, and system-generated input. Database cluster 24 can contain electronic medical records for various patients. Data from these records can be used by the system to generate system-generated input to be populated into sections of electronic clinical documents. For example, images of a patient that may have been captured or stored elsewhere in the system, such as on an image capturing device (not shown), may be populated by the system into an electronic note documenting a particular patient encounter. Further, forms for supporting structured user input may also be generated, at least in part, on the image capturing device itself and stored in database cluster 24, and may be customized by a particular health care provider or institution. And, electronic clinical documents that have been populated with various forms of input can be stored in database cluster 24.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, image capturing devices, microphones, satellite dishes, scanners, or the like. Commands and information may be sent directly from a remote healthcare device to the server 22. In accordance with various embodiments of the present invention, commands and information may also be sent directly from an image capturing device to the server 22, and vice versa. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnections are well known. Accordingly, additional details concerning the internal construction of the server 22 and the remote computers 28 are not further disclosed herein.

Any type of image capturing device, such as the Ricoh Caplio 500 SE, may be used to capture images to be associated with metadata and embedded into electronic clinical documents. Additionally, images may be received by an external image capturing device and then communicated to a remote computer 28 or into the control server 22. For example, a photographer can capture images of a patient with an image capturing device. Information may be added as metadata of and associated with the image. The image can then be communicated to a remote computer 28 or the control server 22. The image and associated metadata can then be embedded into an electronic clinical document, as more fully described below.

The electronic clinical document can be provided via any type of graphical display, such as a computer monitor or any other type of graphical presentation apparatus, such as for example, an LCD screen, a laptop display, or a handheld PDA device. An electronic clinical document can be any type of electronic medical documentation relevant to a particular patient and can be part of an electronic healthcare information technology system. An electronic clinical document can also be a clinical event document relating to a particular clinical event for a patient, including, by way of example only, a patient visit or encounter. By way of example and not limitation, electronic clinical documents may be images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. Electronic clinical documents may be stored within an overall electronic medical chart or electronic medical record associated with a patient.

The format for electronic clinical documents may be customized by the user and/or may be established by a particular healthcare institution, such as by using a profile stored in a database, such as database cluster 24, or by using a locally stored profile on a remote computer (e.g., remote computer 28 of FIG. 1).

"Image", as the term is utilized herein, refers to any type of image (for example, digital photographs, x-rays, ultrasound, and the like) that is captured for the purpose of creating a visual record of information for a patient that can be associated with the electronic clinical document. Clinicians, for example, frequently order images to memorialize relevant image-related information associated with patient interactions, diagnoses, and intended treatment plans. In embodiments of the present invention, images are stored in an electronic format. Any electronic format can be used. Compressed or uncompressed formats can be used and are contemplated as being within the scope of embodiments of the present invention. In other embodiments, images can be stored in an electronic file, transferred to or imported into a medical information system, and then embedded into an electronic clinical document. Any and all such variations and combinations thereof, are contemplated to be within the scope of embodiments hereof.

Typically, if a physician or other provider has additional documentation to add relevant to the image, there is not immediate access to the image file. As such, if the physician desires to review, edit or add to the image related information, the physician must wait until the image is uploaded and directed to the appropriate electronic medical record, which is inefficient and frustrating. However, the image capturing device of the present invention is capable of beginning structured documentation. For example, a clinical form or table which provides pre-defined structure designed for receiving user input relevant to particular aspects of a patient's condition and/or treatment may be used in accordance with embodiments of the present invention. The particular structure used to guide the user's input is communicated to the image capturing device. In embodiments, the structure is communicated via barcode, a memory device, wireless communication, or a combination thereof. The structure defines at least one field, such that information relevant to the particular image is documented. The photographer is prompted, in one embodiment, to input information that is associated with the image as metadata. Any type of clinical information relevant to the patient may be received via structured user input provided that a particular field that is capable of capturing the information is communicated to the image capturing device. As mentioned briefly, the information may be stored as metadata. In one embodiment, at least a portion of the information is stored in an exchangeable image file format (EXIF) header. In one embodiment, at least a portion of the information is stored in the filename.

Figure 2:
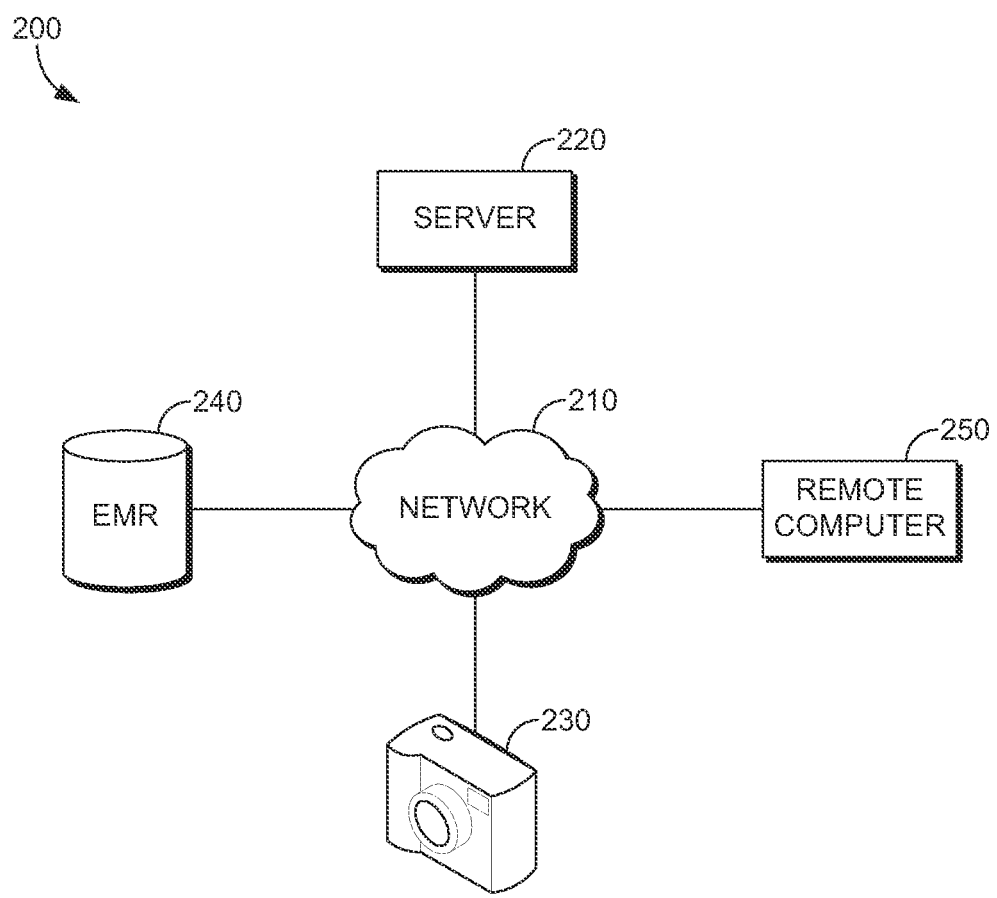
FIG. 2 schematically shows a network environment suitable for performing embodiments of the invention

Referring now to FIG. 2, a block diagram is provided illustrating an exemplary system 200 in which an image acquisition server 220 is shown connected by a network 210 to an an image capturing device 230, EMR 240, and a remote computer 250, in accordance with an embodiment of the present invention. The image acquisition server 220 may be part of a comprehensive computing system within a clinical environment similar to the exemplary computing system 20 discussed above with reference to FIG. 1.

The image acquisition server 220 may include a database (not shown) storing data communicated by the image acquisition device 230. The image acquisition server 220 is comprised of various components, including a monitoring component, a receiving component, an extraction component, an identification component, a storing component, and a displaying component. The monitoring component monitors a repository for at least one image. When an image arrives in the repository, the receiving component receives the image for further processing. An extraction component extracts metadata associated with the image. The extraction component, in one embodiment, also extracts information from the file header. In another embodiment, the extraction component extracts information from the file name. An identification component identifies a patient associated with the metadata and a storing component stores the image and associated metadata in an EMR for the patient. In one embodiment, the identification component identifies the patient with the metadata. In one embodiment, the identification component identifies the patient based on an existing patient to device association. A displaying component displays the image and associated metadata in the EMR. In one embodiment, the displaying component displays the image and associated metadata on a remote computer 250.

In one embodiment, the image acquisition server 220 also includes an encoding component and a communication component. The encoding component encodes a protocol for capturing at least one image of a patient. The protocol is encoded, in one embodiment, in a barcode. The communication component communicates the encoded protocol to the image capturing device.

The image capturing device is comprised of a barcode receiving component, a protocol component, a decoding component, a displaying component, a population component, a capturing component, an association component, and a communication component. The barcode receiving component receives a barcode encoded with information associated with a patient. Information encoded in the barcode is decoded by the decoding component. The information is utilized to begin structured documentation. The protocol receiving component receives a protocol for capturing at least one image of the patient. The protocol comprises orders from a practitioner, a workflow for capturing the at least one image, or a combination thereof. In one embodiment, the protocol is encoded in the barcode and the protocol component receives the protocol from the decoding component. The displaying component displays the protocol for capturing the at least one image of the patient. At least one field is populated with metadata corresponding to the patient with the population component. The capturing component captures the at least one image and the association component associates the metadata with the at least one image. The at least one image and associated metadata is communicated to an electronic medical record associated with the patient by the communication component.

Figure 3:
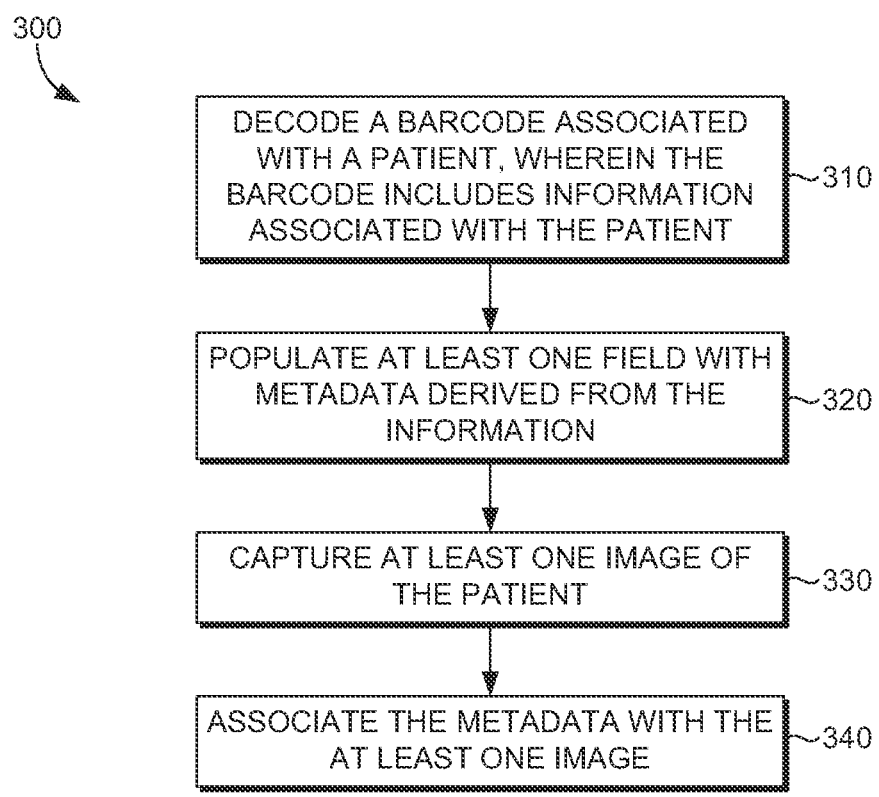
FIG. 3 is a flow diagram showing an exemplary method for populating an at least one field with metadata for association with at least one image, in accordance with an embodiment of the present invention.

With reference to FIG. 3, an exemplary flow diagram representative of a method for populating an at least one field with metadata for association with at least one image in accordance with an embodiment of the present invention is shown and referenced generally by reference numeral 300. Method 300 may be implemented using the above-described exemplary computing system environment (FIG. 1) and, by way of example only, may be utilized by a clinician to populate an electronic clinical document (e.g., an electronic medical record) associated with a patient. The terms "individual", "person", and "patient" are used interchangeably herein and are not meant to limit the nature of the referenced individual in any way. Rather, the methods and systems described herein are equally applicable in, for instance, a veterinary setting. Further, use herein of the term "patient" is not meant to imply any particular relationship between the individual in question and those populating an electronic clinical document associated with the individual.

Initially, as shown at step 310, a barcode associated with a patient is decoded. In one embodiment, an image capturing device includes the necessary components to decode the barcode. The barcode may be in various formats, such as two dimensional or three dimensional. In another embodiment, the barcode is decoded by a component of the medical information system described in FIG. 1 and the resulting decoded information is communicated to the image capturing device. Various forms of communication may be utilized, such as via wireless communication between the decoding component of the medical information system and the image capturing device, via Universal Serial Bus (USB) or similar communication, via a memory device such as a Secure Digital (SD) card, or any other method of communication for transmitting information to or from a peripheral device, such as the image capturing device of this example, and a computing system, such as a server or remote computer. In one embodiment, the image capturing device is in two-way communication with the medical information system.

The barcode includes information associated with the patient. In one embodiment, the information includes patient identifying information. At step 320, at least one field is populated with metadata derived from the information. Accordingly, structured documentation is beginning prior to capturing an image that can be associated, and amended as necessary, with an image. At least one image of the patient is captured, at step 330. Metadata, at step 340, is associated with the at least one image. The image and associated metadata is communicated, in one embodiment, to an EMR associated with the patient. In one embodiment, a field of the at least one field is a placeholder for a tag. The tag is used, in one embodiment, to describe the body part or body parts associated with the image. In one embodiment, the tag is received by barcode, a memory device, wireless communication, manual input, or a combination thereof.

In one embodiment, a protocol is received by the image capturing device. The protocol is received, in various embodiments, by any of the forms of communication described herein, including via barcode. The protocol, in one embodiment, comprises orders from a clinician. The orders provide a determination from or authorization by a clinician that at least one image of a patient needs to be captured. In one embodiment, the protocol comprises a workflow for capturing at least one image. The workflow provides instructions to the photographer to capture the at least one image corresponding to the clinician's orders. The instructions may further provide details regarding information that should be associated with an image. The information may be inputted manually by the photographer into the image capturing device (or any device or peripheral associated with the medical information system) by any form of communication already disclosed.

In one embodiment, a dictionary is received. The dictionary defines a structure for the at least one field. In one embodiment, the dictionary further comprises a protocol. The protocol comprises orders from a practitioner, a workflow for capturing the at least one image, or a combination thereof. In various embodiments, the dictionary is received by barcode, a memory device, by wireless communication, or a combination thereof.

Figure 4:
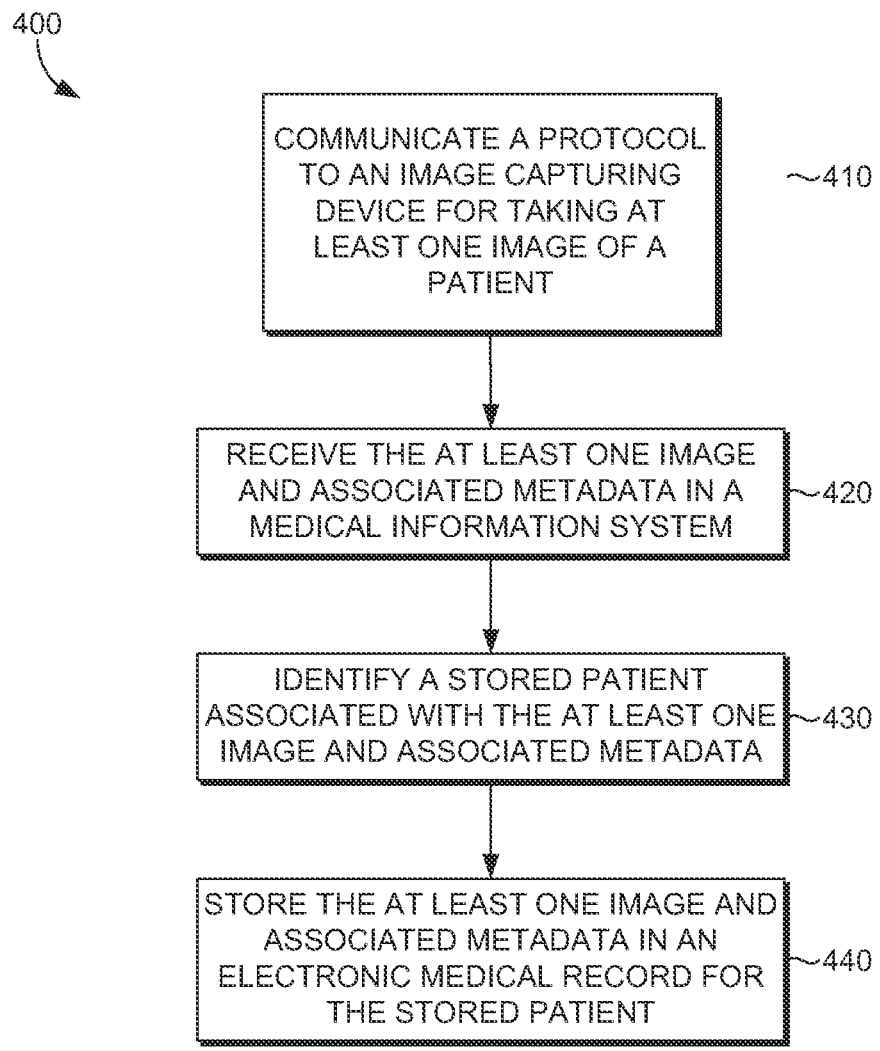
FIG. 4 is a flow diagram showing an exemplary method for communicating a protocol to an image capturing device, in accordance with an embodiment of the present invention.

Referring now to FIG. 4, an exemplary flow diagram representative of a method for communicating a protocol to an image capturing device in accordance with an embodiment of the present invention is shown and referenced generally by reference numeral 400. Method 400 may be implemented using the above-described exemplary computing system environment (FIG. 1) and, by way of example only, may be utilized for protocol driven image acquisition.

Initially, as shown at step 410, a protocol is communicated to an image capturing device for taking at least one image of a patient. The protocol comprises orders from a practitioner, a workflow for capturing the at least one image, or a combination thereof. As briefly described above, the image capturing device is a digital camera, a handheld scanner, or any other imaging device that may be used to capture medical images. At step 420, metadata is associated with the at least one image. The metadata, in various embodiments, is patient identifying information or documentation for clinical or non-clinical purposes relevant to the particular image, and is used to begin structured documentation associated with the image for the patient's EMR. The medical information system receives the at least one image and associated metadata, at step 430. A stored patient is identified corresponding to the at least one image and associated metadata. At step 440, the at least one image and associated metadata is stored in an electronic medical record for the patient.

In one embodiment, a dictionary is communicated to the image capturing device. In various embodiments, the dictionary is communicated by barcode, wireless communication, a memory device, or a combination thereof. The dictionary defines a structure for at least one field for receiving the metadata. Receipt of metadata into the at least one field begins the structured documentation, and once communicated to the electronic medical record, it will be received into the electronic clinical document as defined by the structure. In one embodiment, the dictionary further comprises a workflow. In one embodiment, one field of the at least one field is a tag for describing the body part associated with the image. The tag allows the image to be indexed according to body part. The tag further allows the image to be embedded appropriately in the electronic clinical document. For example, the electronic clinical document may include a silhouette of a human body. The clinician may wish to review any images received by the medical information system for that particular clinical document. Any images with a tag are embedded and appear within the appropriate portion of the silhouette. In one embodiment, the image capturing device is in two-way communication with a medical information system.

In one embodiment, receiving the at least one image and associated metadata in an electronic medical record associated with the patient comprises monitoring a repository for the at least one image and associated metadata. Once the medical information system detects that a new image was received into the repository, the system compares the metadata associated with the at least one image with stored metadata stored in the medical information system. A patient is identified that is associated with the metadata. The at least one image and associated metadata is then transferred to the electronic medical record of the patient.

Figure 5:
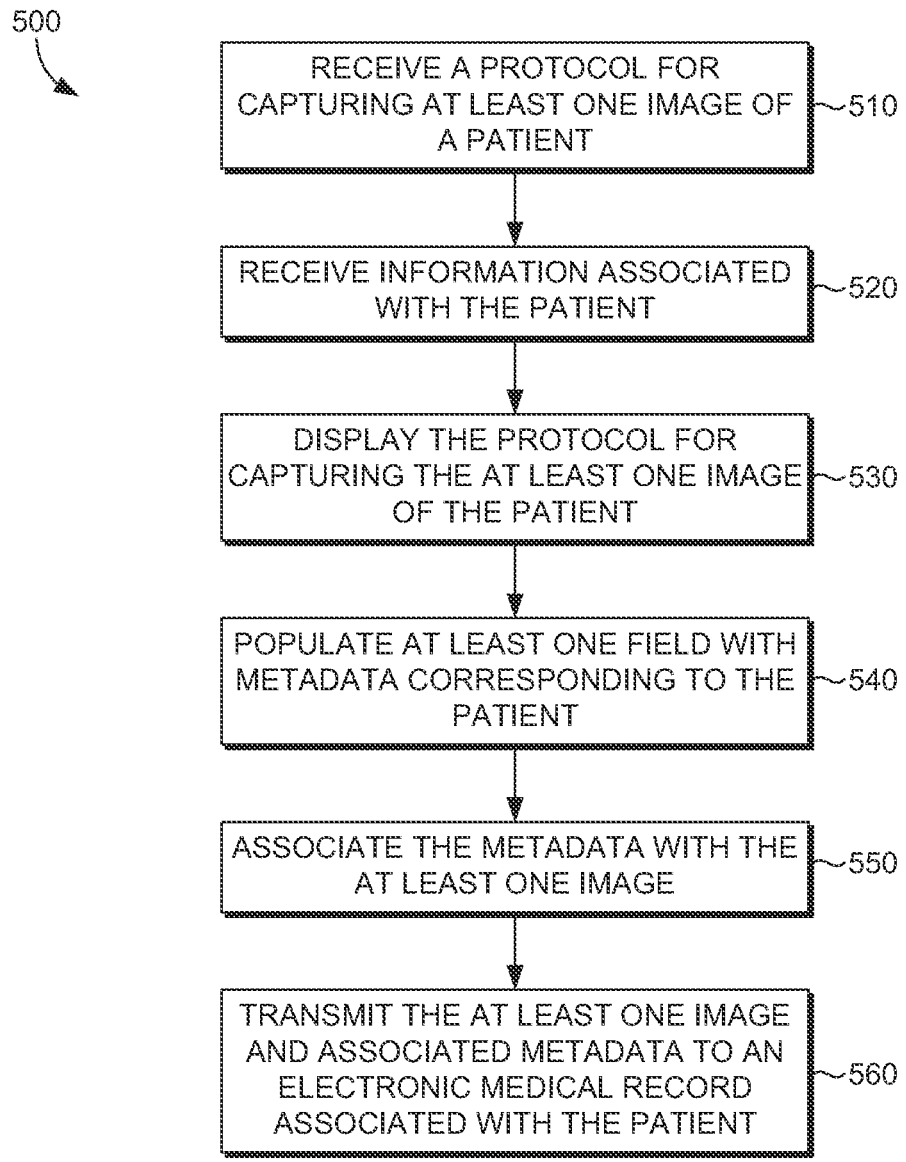
FIG. 5 is a flow diagram showing an exemplary method for receiving a protocol for capturing at least one image of a patient, in accordance with an embodiment of the present invention.

Referring now to FIG. 5, an exemplary flow diagram representative of a method for receiving a protocol for capturing at least one image of a patient, in accordance with an embodiment of the present invention is shown and referenced generally by reference numeral 500. Method 500 may be implemented using the above-described exemplary computing system environment (FIG. 1) and, by way of example only, may be utilized for protocol driven image acquisition.

Initially, as shown at step 510, a protocol for capturing at least one image of a patient is received. The protocol comprises orders from a practitioner, a workflow for capturing the at least one image, or a combination thereof. Information associated with the patient is received, at step 520. The information is utilized to begin structured documentation. At step 530, a protocol is displayed for capturing the at least one image of the patient. At least one field is populated, at step 540, with metadata corresponding to the patient. The metadata is associated with the at least one image at step 550. At step 560, the at least one image and associated metadata is transmitted to an electronic medical record associated with the patient. In one embodiment, a photographer is prompted to input additional information to be associated with the at least one image.

Figure 6:
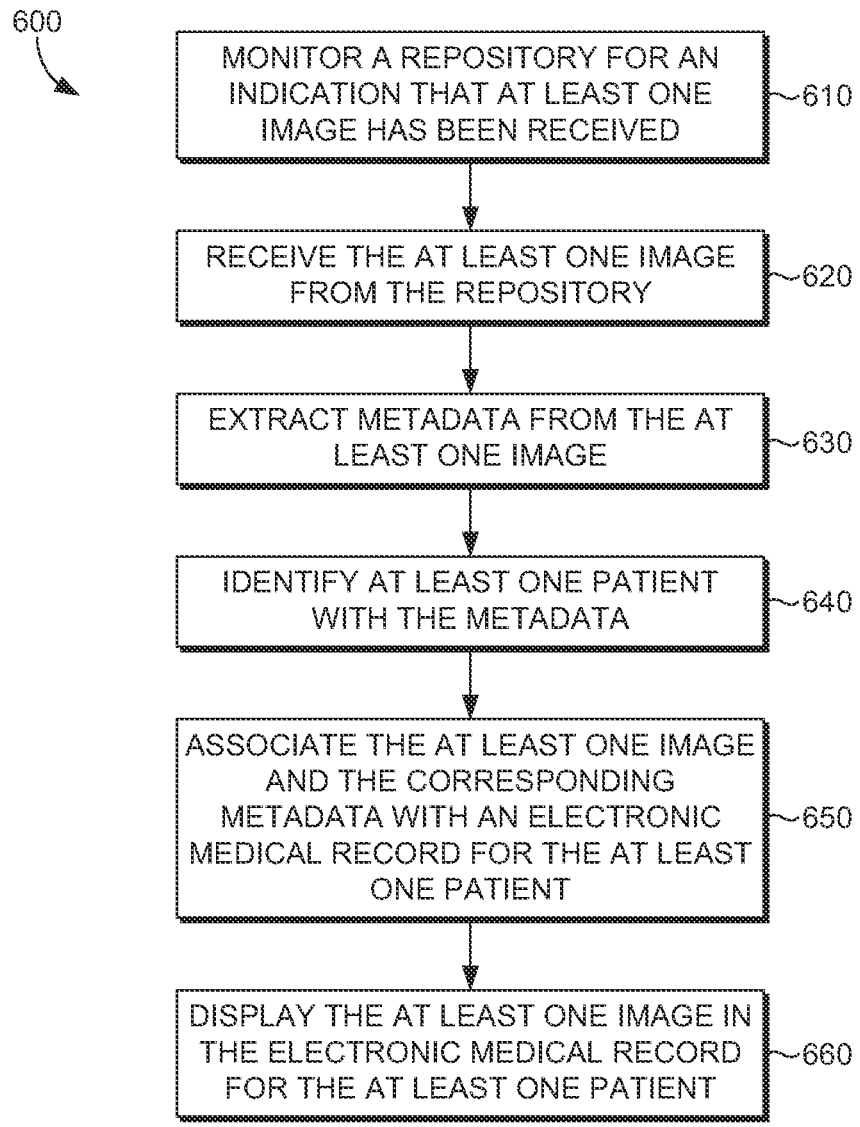
FIG. 6 is a flow diagram showing an exemplary method for receiving images from a repository and associating the images with an EMR for at least one patient, in accordance with an embodiment of the present invention.

Referring now to FIG. 6, an exemplary flow diagram representative of a method for receiving images from a repository and associating the images with an EMR for at least one patient, in accordance with an embodiment of the present invention is shown and referenced generally by reference numeral 600. Method 600 may be implemented using the above-described exemplary computing system environment (FIG. 1) and, by way of example only, may be utilized to prepopulate clinical events with image based documentation.

Initially, as shown at step 610, a repository is monitored for an indication that at least one image has been received. At step 620, the image is received from the repository. Metadata is extracted from the at least one image at step 630. At least a portion of the metadata is included in an EXIF header, in one embodiment. In another embodiment, at least a portion of the metadata is included in the filename. At least one patient is identified, at step 640, with the metadata. At step 650, the at least one image and the corresponding metadata is associated with an electronic medical record for the at least one patient. The at least one image is displayed in the electronic medical record for the at least one patient at step 660.

In one embodiment, a body part associated with the at least one image is identified. In one embodiment, a tag is defined for the at least one image. The tag describes the body part associated with the at least one image and can be used to embed or receive an image within a silhouette in the electronic clinical document. In one embodiment, the tag is stored as metadata of the at least one image.

In one embodiment, clinical documentation is received to associate with the at least one image. The clinical documentation is stored as metadata in any of the forms already described herein. The clinical documentation may include notes from a clinician that were communicated to an image capturing device to be associated with at least one image, documentation from the photographer, and documentation received via barcode, wireless communication, or memory device.

In embodiments, displaying the at least one image in the electronic medical record comprises identifying a body part associated with the at least one image. A tag is defined for the at least one image and stored as metadata. In one embodiment, the at least one image is indexed according to the body part and displayed according to the index. In another embodiment, searching is enabled for at least one image according to the tag.

In embodiments, the at least one image is stored in a standard format. For example, the image may be a JPG, a GIF, a PDF, or a TIFF. In one embodiment, the filename comprises information derived from the metadata. In one embodiment, dictation is associated with the at least one image. In one embodiment, the dictation is available in the electronic medical record for the at least one patient.

Figure 7:
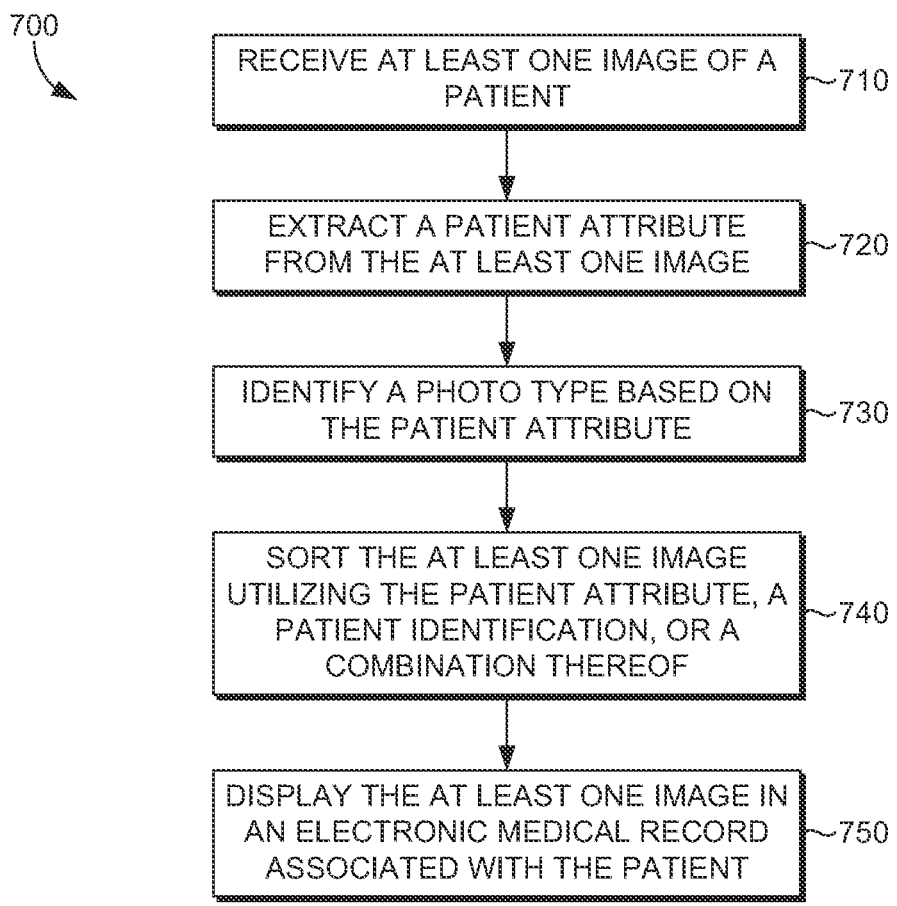
FIG. 7 is a flow diagram showing an exemplary method for sorting and displaying images according to a patient attribute and/or a patient identifier in accordance with an embodiment of the present invention.

Referring now to FIG. 7, an exemplary flow diagram representative of a method for sorting and displaying images according to a patient attribute and/or a patient identifier in accordance with an embodiment of the present invention, in accordance with an embodiment of the present invention is shown and referenced generally by reference numeral 700. Method 700 may be implemented using the above-described exemplary computing system environment (FIG. 1) and, by way of example only, may be utilized to prepopulate clinical events with image based documentation.

Initially, as shown at step 710, at least one image of a patient is received. The image may be in any format, such as those already described herein. A patient attribute is extracted from the at least one image at step 720. The patient attribute includes, in one embodiment, a body part associated with the at least one image. In another embodiment, the patient attribute includes patient identifying information. In yet another embodiment, the patient attribute includes clinical documentation (as described above). At step 730, a photo type is identified based on the patient attribute.

The at least one image is stored, at step 740, utilizing the patient attribute and a patient identification. As mentioned briefly above, the patient identification is derived, in one embodiment, from the patient attribute. In one embodiment, the at least one image is stored in a standard format and the filename comprises the metadata (or at least a portion thereof). In one embodiment, dictation is associated with the at least one image. At step 750, the at least one image is displayed in an electronic medical record associated with the patient.

In one embodiment, a tag is defined for the at least one image. The tag describes the body part associated with the at least one image. In one embodiment, the tag is stored as metadata of the at least one image. As described above, the tag allows the image to be depicted as part of a silhouette in the electronic medical record and allows the clinician to quickly identify images associated with a particular body part.

In one embodiment, displaying the at least one image in the electronic medical record comprises indexing the at least one image, enabling searching for the at least one image according to an index, displaying the at least one image according to the index, or a combination thereof.

Figure 8:
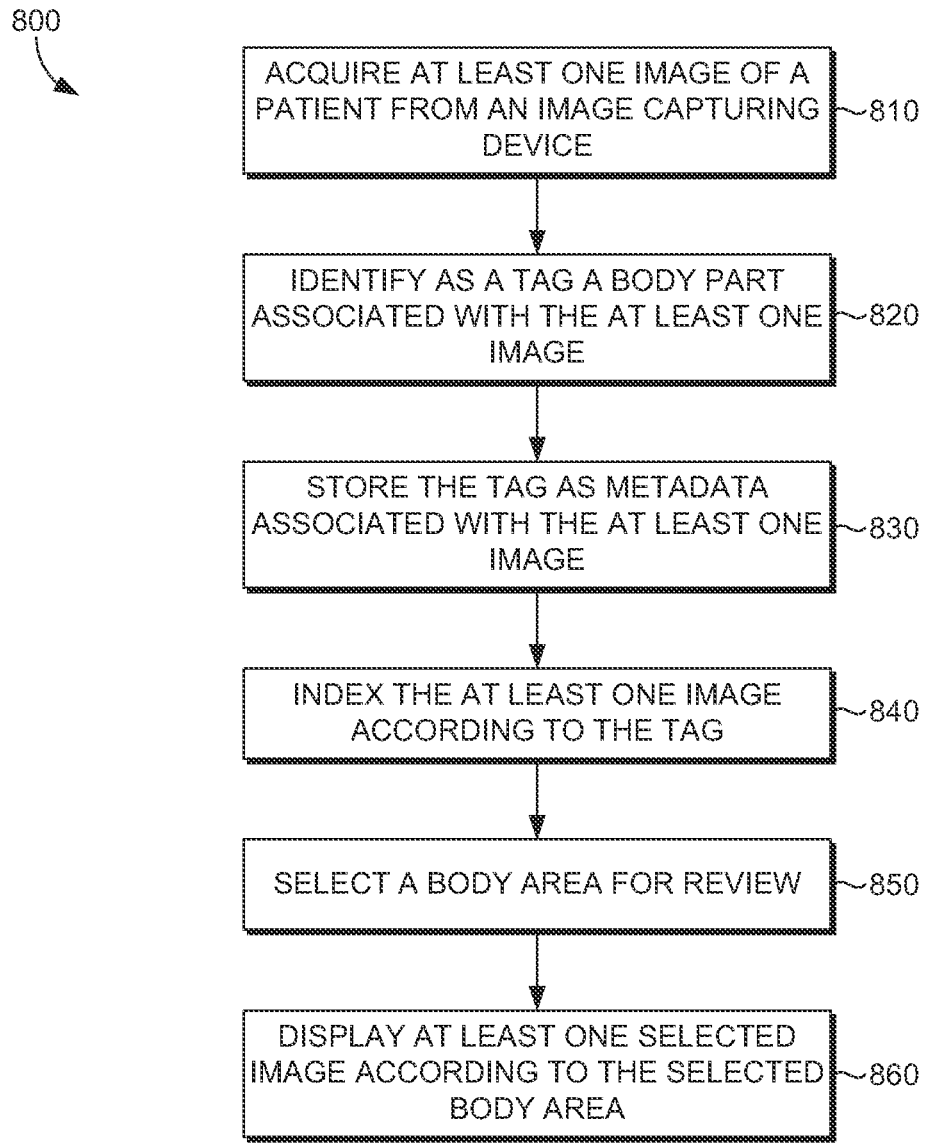
FIG. 8 is a flow diagram showing an exemplary method for indexing at least one image, in accordance with an embodiment of the present invention.

Referring now to FIG. 8, an exemplary flow diagram representative of a method for indexing at least one image, in accordance with an embodiment of the present invention is shown and referenced generally by reference numeral 800. Method 800 may be implemented using the above-described exemplary computing system environment (FIG. 1) and, by way of example only, may be utilized to prepopulate clinical events with image based documentation.

Initially, as shown at step 810, at least one image of a patient is acquired from an image capturing device. At step 820, a body part associated with the at least one image is identified as a tag. The tag is stored as metadata associated with the at least one image at step 830. The at least one image is indexed, at step 840, according to the tag. At step 850, a tag is selected for reviewing a body area. At least one selected image is displayed according to the selected tag at step 860. In one embodiment, clinical documentation to be associated with the at least one image is received.

As can be understood, the present invention provides systems, methods, and user interfaces for protocol driven image acquisition. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

The invention claimed is:

1. One or more computer storage devices having computer-executable instructions embodied thereon, that when executed, perform a method of prepopulating clinical events with image based documentation, the method comprising:
   receiving, by a medical information system, an image of a patient and metadata associated with the image, the image captured by an image capturing device communicatively coupled with the medical information system;
   extracting the metadata, the metadata comprising an identification of the patient and clinical documentation associated with the image;
   creating a tag describing a body part associated with the image, wherein the tag is selectable;
   storing the image, the corresponding metadata, and the tag in an electronic medical record for the patient, wherein the electronic medical record for the patient is within the medical information system and is identified based on the identification of the patient;
   embedding the tag, the image, and the corresponding metadata at a location on a silhouette of a human body corresponding to the body part described by the tag, wherein the silhouette of the human body is a graphical representation of the human body and is included in the electronic medical record for the patient;
   providing, via the electronic medical record, the silhouette of the human body to a clinician device;
   receiving, on the clinician device, a selection of the tag; and
   displaying the image and the associated clinical documentation on the clinician device.

2. The media of claim 1, wherein the image is received in a repository.

3. The media of claim 2, further comprising monitoring the repository for an indication that the image is available.

4. The media of claim 3, further comprising receiving the image from the repository.

5. The media of claim 4, further comprising receiving clinical documentation to associate with the image.

6. The media of claim 1, further comprising indexing the image according to the body part.

7. The media of claim 6, further comprising displaying the image according to an index.

8. The media of claim 1, further comprising enabling searching for the image according to the tag.

9. The media of claim 1, further comprising storing the image in a standard format, wherein a filename comprises information derived from the metadata.

10. The media of claim 1, further comprising associating dictation with the image.

11. One or more computer storage devices having computer-executable instructions embodied thereon, that when executed, perform a method of prepopulating clinical events with image based documentation, the method comprising:
   receiving, by a medical information system, at least one image of a patient and metadata associated with the at least one image, the at least one image captured by an image capturing device communicatively coupled with the medical information system;
   creating a tag for the at least one image, wherein the tag is selectable and describes a body part depicted in the at least one image;
   extracting a patient attribute and clinical documentation from the metadata;
   storing the at least one image, the clinical documentation, and the tag in association with the patient attribute in an electronic medical record for the patient within the medical information system;
   embedding the tag, the at least one image, the patient attribute, and the clinical documentation in a location on a silhouette of a human body corresponding to the body part described by the tag, wherein the silhouette of the human body is a graphical representation of the human body and is included in the electronic medical record;
   displaying the silhouette of the human body, including the tag, at a clinician device;
   receiving, at the clinician device, a selection of the tag; and
   displaying the at least one image and the clinical documentation on the clinician device.

12. The media of claim 10, wherein the dictation is available in the electronic medical record for the patient.

13. The media of claim 11, wherein the patient attribute includes a body part associated with the at least one image.

14. The media of claim 13, wherein displaying the at least one image comprises indexing the at least one image according to the body part.

15. The media of claim 11, wherein the patient attribute includes clinical documentation.

16. The media of claim 11, wherein the patient attribute identifies a photo type.

17. The media of claim 11, further comprising associating dictation with the at least one image.

18. A computerized system for prepopulating clinical events with image based documentation, the system comprising:
   one or more processors coupled to a computer storage device, the computer storage device having stored thereon a plurality of computer software components executable by the processor, the computer software components comprising:
     an extraction component for extracting metadata associated with an image of a patient acquired from an image capturing device, the metadata including clinical documentation that was communicated via an electronic medical record of the patient to the image capturing device or received as structured user input received at the image capturing device;
     a tagging component that creates a tag for an image, the tag describing a body part associated with the image, wherein the tag is configured to be selectable;
     a storing component that:
       stores the image and the associated metadata in the electronic medical record for the patient, the associated metadata including the tag, and
       embeds the tag, the image, and the associated metadata in a location on a silhouette of a human body corresponding to the body part described by the tag, wherein the silhouette of the human body is a graphical representation of the human body and is included in the electronic medical record for the patient; and
     a displaying component for displaying, via a clinician device, the image and the associated metadata depicted on the silhouette of a human body in accordance with the tag.

19. The media of claim 14, further comprising enabling searching for the at least one image according to an index.

20. The system of claim 18 further comprising:
a monitoring component that monitors a repository for the image;
an identification component that identifies a patient associated with the metadata;
an encoding component for encoding a protocol; and
a communication component for communicating the protocol to an image capturing device.

* * * * *